United States Patent [19]

Blumenthal

[11] Patent Number: 4,462,111

[45] Date of Patent: Jul. 24, 1984

[54] APPARATUS AND METHOD FOR EXAMINING A BODY, PARTICULARLY USEFUL IN TOMOGRAPHY

[75] Inventor: Rafael Blumenthal, Kiriat Tivon, Israel

[73] Assignee: Elscint Incorporated, Boston, Mass.

[21] Appl. No.: 382,578

[22] Filed: May 27, 1982

[51] Int. Cl.³ .............................................. A61B 6/00
[52] U.S. Cl. ....................................... 378/014; 378/11
[58] Field of Search ......................... 378/27, 14, 4, 11; 250/363 S

[56] References Cited

U.S. PATENT DOCUMENTS

| | | | |
|---|---|---|---|
| 2,133,738 | 10/1938 | Chaoul | 378/27 |
| 2,967,939 | 1/1961 | Caha et al. | 250/363 S |
| 3,928,769 | 12/1975 | Smith | 378/27 |
| 3,986,031 | 10/1976 | Chekroun | 378/11 |
| 4,010,371 | 3/1977 | Le May | 378/14 |

Primary Examiner—Alfred E. Smith
Assistant Examiner—T. N. Grigsby
Attorney, Agent, or Firm—Sandler & Greenblum

[57] ABSTRACT

Apparatus for examining a body, particularly useful in tomography, for producing transverse sectional images of the body, comprises scanning means supported by a carriage coupled to its mounting via a pair of links defining, with the carriage and its mounting, a four-link, parallel-motion mechanism which, upon oscillation of the links, effects a curvilinear movement of the carriage with respect to the body, and thereby a curvilinear traverse of the body by the scanning means. The carriage is also rotatably mounted on the machine frame enabling the carriage, and the scanning means supported thereon, also to be rotated about the body either incrementally or continuously.

20 Claims, 3 Drawing Figures

APPARATUS AND METHOD FOR EXAMINING A BODY, PARTICULARLY USEFUL IN TOMOGRAPHY

BACKGROUND OF THE INVENTION

The present invention relates to a method and apparatus for examining a body. The invention is particularly useful in tomography for producing transverse sectional images of the body being examined, and is therefore described below with respect to this application.

Computerized axial tomographic (hereinafter called "CAT") apparatus is known which reconstructs an image of a body being examined by rotating a source of penetrating radiation, e.g., X-rays, completely around the body. Typical apparatus includes a carriage, generally in the form of a U-shaped yoke. The radiation source is supported on one leg of the yoke, and the detector means on the other leg, the yoke being driven through a plurality of linear (i.e., rectilinear) traverses, each at a different angular position with respect to a circle, known as the circle of reconstruction within which the body to be examined is located. Some apparatus, known as LRM (linear-rotational-mode) apparatus, may be operated both according to the above linear mode and also according to a rotational mode to provide a fast rotational traverse of the radiation source and detector means around the circle of reconstruction within which the examined body is located.

It is critical to maintain a fixed spatial relationship between the radiation source and the detector means during their traverse of the examined body. For this reason, existing LRM apparatus usually includes a plurality of high-precision parallel slides guiding the linear movement of the carriage. Such slides are expensive to provide, and time-consuming to align.

In addition, the radiation from the source in such apparatus is usually of a fan-beam shape. The length of each traverse of the carriage must therefore be sufficient for the fan-beam to clear the circle of reconstruction while travelling at a constant velocity and while also providing sufficiently for stop and reverse motions for the carriage. Accordingly, the length of traverse of the carriage must increase with fan angle, source distance from center, and linear speed. Since each linear traverse is made at a different angular position around the examined body, the apparatus must necessarily be of large size to enable the carriage to clear the ground at the extreme angular positions of the carriage.

Because of the foregoing and other considerations, the CAT apparatus, particularly of the LRM type now in use, is designed according to a compromise between speed and size, high speed being desirable in order to reduce the scanning time but also requiring bulky constructions expensive to produce, difficult to maintain and noisy in operation.

BRIEF SUMMARY OF THE INVENTION

An object of the present invention is to provide apparatus and method for examining a body having advantages in the above respects. Another object of the invention is to provide the above advantages in apparatus and method particularly useful in CAT equipment to reconstruct an image by translating and rotating a source of penetrating radiation with respect to the examined body.

According to a broad aspect, the invention provides a method and apparatus of scanning or examining a body, and particularly for producing transverse sectional images of the body, by scanning means driven by a four-link, parallel-motion mechanism to effect a curvilinear, rather than a rectilinear, traverse of the body by the scanning means.

According to a more specific aspect of the invention, there is provided apparatus for examining a body including scanning means for scanning the body along a plurality of lines (e.g., by a fan-shaped beam) through the body, a carriage for supporting the scanning means, and drive means for driving the carriage with respect to the body to effect the scanning thereof by the scanning means, characterized in that the drive means includes a pair of links and means for oscillating the links; and in that said links are pivotably mounted at one of their ends to spaced points of a common mounting member, and are pivotably coupled at their opposite ends to spaced points of the carriage, with the distance between the pivot points of one link being equal to that of the other, and the distance between the pivot points on the mounting member being equal to that between the pivot points on the carriage. Thus, the arrangement is such that the links define, with the mounting member and the carriage, a four-link, parallel-motion mechanism which, upon oscillation of the links, effects a curvilinear movement of the carriage with respect to the mounting member, and thereby a curvilinear traverse of the body by the scanning means, without altering the angles of the scanning lines through the body during the curvilinear traverse of the scanning means.

In the preferred embodiment of the invention described below, the common mounting member is rotatably mounted on a static frame, the drive means also including means for rotating the mounting member, and thereby also the carriage and scanning means, about the body. The mounting member may be rotated either in incremental steps, to index the carriage around the body before each curvilinear traverse, or continuously (during a rotational mode of operation) to provide a fast rotational orbit of the carriage.

The invention is particularly useful in tomographic apparatus, and especially in LRM-CAT apparatus, wherein the carriage is formed with an opening for receiving the body to be scanned, the body scanning means including a source of penetrating radiation carried on the carriage on one side of said opening, and detector means carried by the carriage on the opposite side of said opening to detect the radiation passing through the body being scanned.

The invention provides a number of advantages particularly when implemented in CAT apparatus including a radiation source producing a fan-shaped beam. One important advantage is that the described arrangement permits the construction of a closed carriage of reasonable dimensions. This is because the linear distance between the end points of travel of the source of a fan-shaped beam moving in a circular path concentric with the circle of radiation is smaller than that moving in a straight line path, when the requirement of clearing the circle is to be met; this difference in the linear distance increases with the fan angle. Thus, the described arrangement permits the carriage to completely enclose the opening in which the examined body is located while still maintaining reasonable dimensions of the carriage, thereby permitting not only size reduction, but also increased rigidity of the carriage for a given size. This arrangement also obviates the need for expensive slides in order to maintain the critical fixed relationship between the radiation source and the detector during their traverse of the examined body. In addition, the described arrangement permits larger fan angles to be employed, thereby reducing the scanning time by reducing the number of traverses. A still further advantage in the described arrangement is that it enables the use of simpler and less expensive drives and controls, thereby further decreasing the overall cost of producing and maintaining the equipment.

While the invention is particularly useful in CAT equipment in which the radiation source is disposed externally of and projected through the examined body, it will be appreciated that the invention, or features thereof, could also be advantageously used in positron-emission tomography (PET), wherein the penetrating radiation originates within the body itself, e.g., by using gamma cameras which detect radiation emitted from radioactive tracer elements introduced into the examined body.

Further features and advantages of the invention will be apparent from the description below.

BRIEF DESCRIPTION OF THE DRAWINGS

The invention is herein described, somewhat diagrammatically and by way of example only, with reference to the accompanying drawings, wherein.

DESCRIPTION OF A PREFERRED EMBODIMENT

Figure 1:
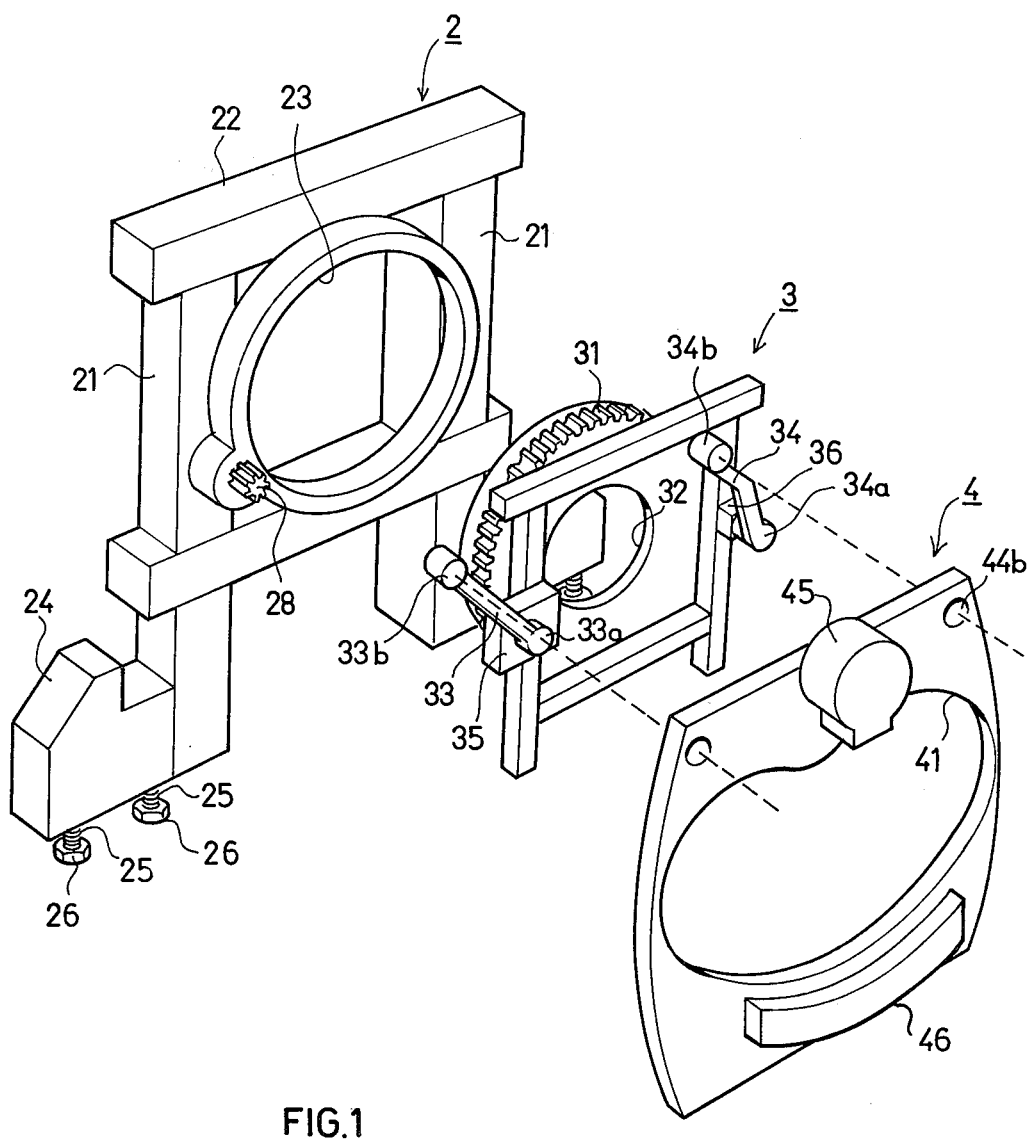
FIG. 1 is a three-dimensional view illustrating one form of apparatus constructed in accordance with the present invention.

The apparatus illustrated in the drawings is a CAT machine for producing transverse sectional images of a body by means of penetrating radiation, such as by a fan-shaped beam of X-rays, to obtain the distribution of the absorption coefficients with respect to the radiation in planes passing through the body. The illustrated apparatus is capable of being operated either according to a curvilinear mode, to effect curvilinear traverses of the radiation source and detectors with respect to the examined body (as distinguished from rectilinear traverses as in existing LRM equipment); or according to a rotational mode, to effect rotational orbits of the radiation source and detectors with respect to the examined body. It can therefore be called a CRM (Curvilinear-Rotational-Mode) apparatus.

Figure 2:
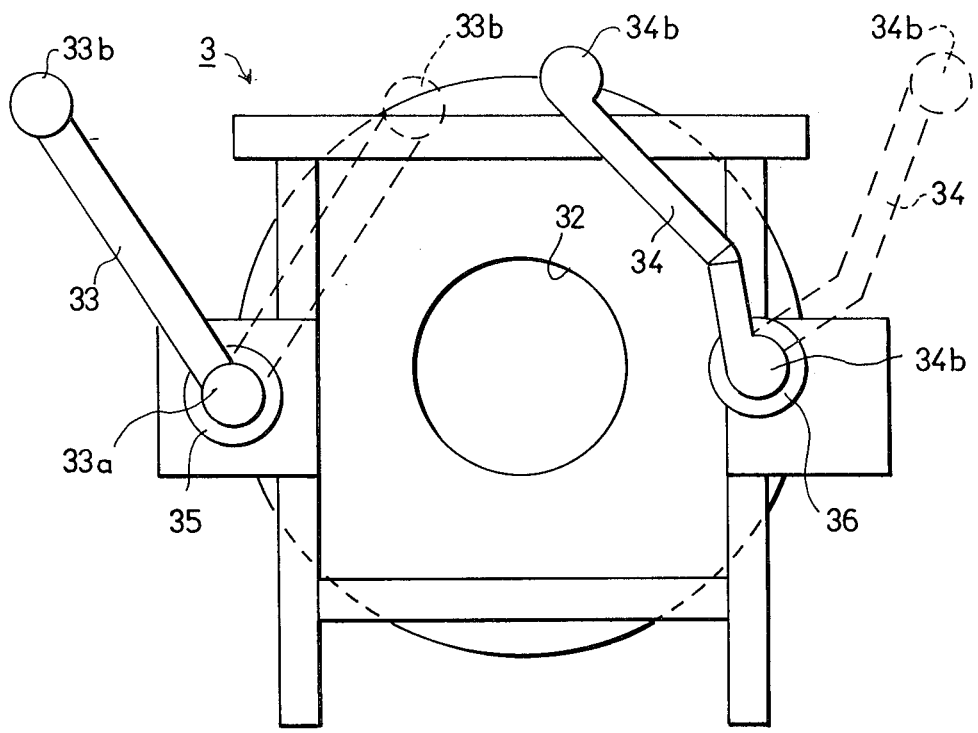
FIG. 2 is a front view illustrating only the rotary and oscillatory mounting for the carriage supporting the radiation source and the detectors in the apparatus of FIG. 1.
Figure 3:
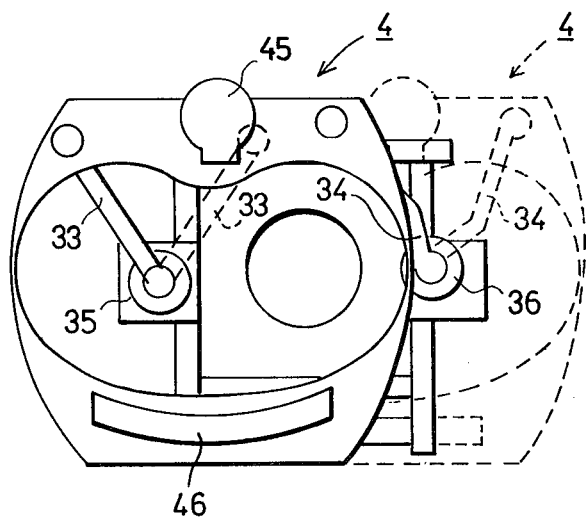
FIG. 3 is a front view of the apparatus of FIG. 1 illustrating the carriage, in solid lines when in one extreme position of its curvilinear traverse of the examined body, and, in broken lines, when in the opposite extreme position of its curvilinear traverse of the examined body.

Briefly, the illustrated equipment includes three basic components, namely: a static frame or gantry, generally designated 2; a rotary intermediate mounting, generally designated 3 and best illustrated in FIG. 2, rotatably mounted to the static frame 2; and a carriage, generally designated 4, for supporting the radiation source and detector array for curvilinear movement (as distinguished from rectilinear movement in the conventional CAT apparatus) with respect to the body being examined. A curvilinear scan of the body is effected by driving carriage 4 through its curvilinear path, as will be described more particularly below. The intermediate mounting 3 is rotated one angular increment, approximately equal to the fan angle, between each curvilinear scan in order to position carriage 4, and thereby the radiation source and detector array carried thereby, at different angular positions with respect to the examined body during the curvilinear scans. In addition, intermediate mounting 3 may also be continuously rotated to produce a fast rotational scan of the examined body during a rotational mode of operation of the apparatus, i.e., without a curvilinear scan.

More particularly, the static frame or gantry 2 may be of any conventional construction, including vertical columns 21 and horizontal beams 22 joined together in any suitable manner to form a rigid frame formed with a central opening 23 for the body to be examined. The static frame 2 is mounted on legs 24, each including jack screws 25 carrying base plates or feet 26 to permit precise adjustment or tilting of the static frame with respect to the supporting surface.

The static frame 2 further supports a rotary motor, schematically indicated at 27, driving a pinion 28 for rotating the intermediate mounting 3. The latter mounting is rotatably mounted in any suitable manner on the static frame 2 and is rotated with respect to the frame by pinion 28 (FIG. 1) meshing with teeth 31 formed around the circumference of mounting 3, as in existing apparatus.

The intermediate mounting 3 also carries a linkage mechanism for supporting the carriage 4 and for causing it to be driven in a curvilinear manner with respect to the static frame 2 and mounting 3, and thereby with respect to the examined body located within opening 32 of the mounting.

For this purpose, the rotary intermediate mounting 3 is provided with a pair of equal-length links 33, 34 pivotably coupled at one of their ends 33a, 34a to the mounting 3, and also pivotably coupled at their opposite ends 33b, 34b to the carriage 4. The pivotable couplings of the links 33, 34 to mounting 3 and carriage 4 are at equally-spaced points; i.e., the distance between pivot points 33a, 33b is equal to that between pivot points 34a, 34b, and the distance between pivot points 33a, 34a is equal to that between pivot points 33b, 34b. Thus, the two links 33 and 34 define, with the mounting member 3 and the carriage 4, a four-link, parallel-motion mechanism, in which the line on carriage 4 connecting pivot points 33b, 34b of the two links 33, 34 always moves so that it is parallel to the line on the mounting 3 connecting the pivot points 33a, 34a of the two links, and in which link 33 (i.e., the line connecting its pivot points 33a, 33b) always moves so that it is parallel to link 34 (i.e., the line connecting its pivot points 34a, 34b). The carriage 4 as a unit, however, moves through a curvilinear path whose radius of curvature is equal to the distance between pivot points 33a, 33b (and between pivot points 34a, 34b).

In order to drive the carriage 4 through its curvilinear path, the mounting 3 is provided with a pair of oscillating actuators or motors 35, 36, one for each of the links 33, 34, for oscillating the links about their respective pivot points 33a, 34a. It will be appreciated that a common actuator or motor could be provided for both links 33, 34. FIG. 2 illustrates in solid lines, and in broken lines, respectively, the two extreme positions of the links during their oscillation by motors 35, 36.

The carriage 4 is pivotably mounted at pivot points 43b, 44b, respectively, to the ends of the two links 33, 34 of mounting 3, these carriage pivot points corresponding to pivot points 33b, 34b of the links.

Carriage 4 is also formed with an opening 41 for receiving the body being examined. Whereas the carriage in the previously-known CAT apparatus was generally in the form of a U-shaped yoke so that the body-receiving opening was open at one side because of the rectilinear movement of the carriage, in the present case the body-receiving opening 41 is totally enclosed by the carriage, this being permitted by the savings in space resulting from the curvilinear movement of the carriage with respect to the examined body. Opening 41 in carriage 4 is preferably of kidney-bean shape, as illustrated, because of this curvilinear movement of the carriage with respect to the examined body, this shape of opening corresponding to the relative curvilinear displacement of the fixed body with respect to the moving carriage, and thereby producing a maximum rigidity in the carriage 4 for this curvilinear movement.

The source of penetrating radiation 45, e.g., an X-ray generator tube, is carried by carriage 4 at one side of opening 41 and centrally thereof. The detector array 46 is carried at the opposite side of opening 41 so as to receive the radiation passing through the examined body received within the opening and thereby to detect the attenuation suffered by the radiation caused by the examined body.

It will be seen that the illustrated apparatus may be operated either according to a curvilinear rotational mode (CRM), as distinguished from the linear rotational mode (LRM) of the prior apparatus, or according to a rotational mode (RM).

When operated according to a curvilinear rotational mode (CRM), the oscillating motors 35, 36 are actuated to drive the links 33, 34 and thereby, because of the four-link, parallel-motion mechanism defined by these links as described above, to drive carriage 4 through a curvilinear path with respect to the examined body received within opening 41 of the carriage. Thus, the radiation source 45 and the detector array 46 both effect a curvilinear traverse of the examined body, first in one direction at one angular position of the carriage, and then in the opposite direction at the next angular position of the carriage.

The radiation source 45 produces a fan-shaped beam in which the radiation fans-out from the point source along a plurality of lines, according to the fan angle, towards the detector array 46 on the opposite side of the carriage 4. It will be appreciated that the curvilinear movement of the carriage 4 with respect to its mounting member 3, and thereby the curvilinear traverse of the body by the radiation source 45, effected by the four-link, parallel-motion mechanism including links 33 and 34 as described above, does not alter the angles of the scanning lines through the body, but rather assures that all the scanning lines move in a parallel direction through the body during the curvilinear traverse.

Between each curvilinear traverse, rotary mounting 3 is rotated a predetermined angular increment so that each curvilinear traverse of the examined body is effected at a different angular position with respect to the examined body, such that sufficient curvilinear traverses are made so as to scan substantially 180° around the examined body.

In order to operate the apparatus according to the fast rotational mode, it is only necessary to rotate mounting 3 by actuation of rotary motor 27 driving pinion 28 meshing with the outer circumferential 31 of the mounting, as in existing apparatus.

It will be appreciated, however, that the apparatus illustrated in the drawings provides a number of advantages over the existing apparatus. Thus, the illustrated apparatus obviates the need for the high-precision parallel slides required in conventional LRM machines for achieving the linear motion with very high mechanical accuracy in the critical spatial relationship between the radiation source and the detectors. In addition, the illustrated apparatus can be constructed of substantially smaller size than the existing equipment, since the curvilinear traverse produced by the carriage not only permits the body-receiving opening to be completely enclosed by the carriage, thereby adding rigidity to the carriage for a given size, but also avoids the large dimensions necessary in the existing equipment to enable the corners of the carriage to be cleared at extreme angular carriage positions. In short, the illustrated construction inherently permits higher-speed operation to shorten the exposure periods, increased fan angles to decrease the number of exposures, simpler installation and maintenance, and quieter operation, when compared to conventional LRM equipment involving rectilinear scans.

While the invention has been described with respect to one preferred embodiment, it will be appreciated that the invention or features thereof could also be used in many other scanning applications (e.g., in PET or gamma cameras as mentioned earlier) involving the examination of an area or region point by point in a continuous systemmatic manner by repeatedly sweeping across the examined area or region until it is completely covered.

What is claimed is:

1. A method for scanning a body located in a static frame wherein the scanning regimen involves angular rotation of a scanning head about the body from a first to a second angular position, and curvilinear translation of the scanning head in a plane perpendicular to the axis of rotation of the scanning head about the body while the scanning head is in a fixed angular position.

2. The method according to claim 1, wherein said scanning head detects radiation passing through or originating within the body.

3. The method according to claim 2, wherein said scanning head projects penetrating radiation through said body from one side thereof and detects the radiation exiting from the opposite side of the body to thereby measure the attenuation suffered by the radiation in passing through the body.

4. The method according to claim 1, wherein said body is scanned by X-rays.

5. Apparatus for examining a body comprising:
   (a) a static frame;
   (b) an intermediate member rotatably mounted on said frame;
   (c) a carriage having a source for producing penetrating radiation, and means for detecting penetrating radiation from said source; and
   (d) means mounting said carriage on said intermediate member for effecting curvilinear translation of said carriage relative to said intermediate member in a plane perpendicular to the axis of rotation of the intermediate member on said frame.

6. Apparatus according to claim 5 wherein said carriage is formed with an opening for receiving the body to be examined, said source being mounted on said carriage on one side of the opening and said detector means being mounted on the carriage on the opposite side of said opening.

7. Apparatus according to claim 6, wherein said carriage completely encloses said opening on all its sides.

8. Apparatus according to claim 7, wherein said opening is of substantially kidney-bean shape.

9. Apparatus according to claim 5 wherein said means mounting said carriage on said intermediate member includes a pair of links each of which has one end pivotably connected to respective spaced points on said carriage, the other ends of said pair of links being pivotally mounted to respective spaced points on said intermediate member such that curvilinear movement of the carriage is effected relative to the intermediate member when said links are oscillated, and means for imparting oscillating movement to said links.

10. Apparatus according to claim 9 wherein said means mounting said intermediate member is constructed and arranged to effect rotation of said intermediate member on said frame, and said apparatus also includes means for rotating said intermediate member.

11. Apparatus according to claim 10 wherein said carriage is formed with an opening for receiving the body to be examined.

12. Apparatus according to claim 10, wherein said carriage is formed with an opening for receiving the body to be examined, a source of penetrating radiation being supported on said carriage on one side of said opening, and said detector means being supported by said carriage on the opposite side of said opening to detect the radiation passing through the body being scanned.

13. Apparatus according to claim 5, wherein said intermediate member is rotatably mounted on said static frame, said apparatus further including drive means for incrementally or continuously rotating said intermediate member and thereby also said carriage about the body.

14. Apparatus according to claim 13, wherein a source of penetrating radiation is supported on said carriage on the side of said body opposite to that of the detector means.

15. Apparatus according to claim 14, wherein said carriage is formed with an opening for receiving the body to be scanned, said opening being completely enclosed by said carriage.

16. Apparatus according to claim 15, wherein said opening is of substantially kidney-bean shape.

17. Tomographic apparatus for examining a body, and particularly for producing transverse sectional images of the body, comprising:
a static frame;
a rotary mounting member rotatably mounted on said static frame;
a carriage mounted on said rotary mounting member, said carriage including an opening for receiving the body to be scanned;
scanning means carried by said carriage for scanning the body received within said opening of the carriage along a plurality of scanning lines assuming a fan-shaped configuration;
rotary drive means for incrementally or continuously rotating said mounting member with respect to said static frame;
and oscillating drive means for oscillating said carriage with respect to said rotary mounting member;
said oscillating drive means including a pair of links and means for oscillating said links;
said links being pivotably mounted at one of their ends to spaced points of said rotary mounting member, and being pivotally coupled at their opposite ends to spaced points of said carriage, with the distance between the pivot points of one link being equal to that of the other, and the distance between the pivot points on said rotary mounting member being equal to that between the pivot points on said carriage, such that the links define, with the rotary mounting member and the carriage, a four-link, parallel-motion mechanism which, upon oscillation of said links, effects a curvilinear movement of the carriage with respect to said mounting member, and thereby a curvilinear traverse of said body by the scanning means, without altering the angles of said scanning lines through the body during said curvilinear traverse thereof; while said rotary drive means, upon actuation thereof, effects a rotary traverse of the body by said scanning means.

18. Apparatus according to claim 17, wherein said opening in the carriage is enclosed on all sides by said carriage, said scanning means including a source of penetrating radiation carried on said carriage on one side of said opening, and detector means carried on said carriage on the opposite side of said opening to detect the radiation passing through the body being scanned.

19. Apparatus according to claim 18, wherein said opening in the carriage is of substantially kidney-bean shape.

20. Apparatus according to claim 18, wherein said source of penetrating radiation is an X-ray generator.

* * * * *